United States Patent [19]
Infeld et al.

[11] B  3,989,830
[45] Nov. 2, 1976

[54] STABILIZATION OF COPPER COMPLEXES OF 6-METHOXY-1-PHENAZINOL 5,10-DIOXIDE

[75] Inventors: Martin Howard Infeld, Montclair; Harold Leon Newmark, Maplewood, both of N.J.

[73] Assignee: Hoffmann-La Roche Inc., Nutley, N.J.

[22] Filed: Aug. 1, 1974

[21] Appl. No.: 493,955

[44] Published under the second Trial Voluntary Protest Program on March 9, 1976 as document No. B 493,955.

Related U.S. Application Data

[63] Continuation of Ser. No. 141,382, May 7, 1971, abandoned.

[52] U.S. Cl. ................................. 424/245; 424/294
[51] Int. Cl.² ...................................... A61K 31/555
[58] Field of Search ............................ 424/245, 294

[56]            References Cited
        UNITED STATES PATENTS
3,586,674   6/1971   Leimgruger et al. ............... 424/245

OTHER PUBLICATIONS
Gregory, T., "Uses & Applications of Chem. & Related Materials" (1939).

*Primary Examiner*—V. D. Turner
*Attorney, Agent, or Firm*—Samuel L. Welt; Bernard S. Leon; William M. Farley

[57]            ABSTRACT

Stabilization of the copper II complex of 6-methoxy-1-phenazinol 5,10-dioxide, when used in a variety of dosage forms, is achieved by the addition of a 2–20% molar excess of copper ions to the specific dosage form.

8 Claims, No Drawings

STABILIZATION OF COPPER COMPLEXES OF 6-METHOXY-1-PHENAZINOL 5,10-DIOXIDE

This is a continuation, of application Ser. No. 141,382 filed May 7, 1971 now abandoned.

BACKGROUND OF THE INVENTION

Copper II complexes of 6-methoxy-1-phenazinol 5,10-dioxide generally are prepared by combining a solution of 6-methoxy-1-phenazinol 5,10-dioxide (myxin) with a solution of a copper II salt. The precursor, 6-methoxy-1-phenazinol 5,10-dioxide, is readily prepared by selective alkylation of iodinin (1,6-phenazinediol 5,10-dioxide) as, for example, by treating the monosodium salt of iodinin with an alkylating agent such as di-methyl sulfate in an inert organic solvent. A solution of 6-methoxy-1-phenazinol 5,10-dioxide when combined with a solution of a cupric salt, e.g., cupric acetate, forms a copper complex containing one mole of copper for every two moles of 6-methoxy-1-phenazinol 5,10-dioxide. Other suitable cupric salts include those of weak acids having pKa's of about 4.2 or higher such as the lower alkanoic acids, e.g., acetic acid or propionic acid and benzoic acid. The salts of mineral acids, such as cupric sulfate, can also be used but they must be used in buffered solvent systems to avoid highly acidic conditions.

Chemically, copper can exist in ionized form in two combining states - the reduced state, i.e., cuprous or copper I, having a valence of $^{+1}$ and the oxidized state, i.e., cupric or copper II, having a valence of $^{+2}$.

This reaction can be carried out at room temperature or temperatures above room temperature can be used to facilitate solution of the reactants and reduce the amount of solvent needed. Since it is desirable to precipitate the final product from the reaction medium, it is preferred to utilize a solvent or solvent mixture in which both the 6-methoxy-1-phenazinol 5,10-dioxide and the cupric salt are more soluble than the complex formed by their reaction. Exemplary organic solvents which can be conveniently employed include acetonitrile, dimethyl formamide, methanol, ether, chloroform, etc.

The copper II complex of 6-methoxy-1-phenazinol 5,10-dioxide has a high degree and wide spectrum of anti-microbial activity in both in vitro studies and in vivo topical infections. In particular, the copper complex has demonstrated a high level of activity against a wide variety of both gram positive and gram negative bacteria, fungi, protozoa and helminths. This wide spectrum of anti-microbial activity has manifested itself by the efficacy of the copper complex as a chemotherapeutic agent in combatting topical infections.

The copper complex of 6-methoxy-1-phenazinol 5,10-dioxide is physically unsuitable for use alone, i.e., without suitable excipients, in the treatment of topical microbial infections. However, the copper complex, when used in certain topical formulations, i.e., creams and suspensions, while efficacious, is unstable on storage.

There is thus a need for a method of stabilizing such compositions.

BRIEF SUMMARY OF THE INVENTION

This invention relates to a method of stabilizing pharmaceutically acceptable formulations containing the copper II complex of 6-methoxy-1-phenazinol 5,10-dioxide, hereinafter referred to as copper myxin, by the addition of an excess of copper II ions to the formulations.

DETAILED DESCRIPTION OF THE INVENTION

It has been discovered that the addition of excess copper II ions to a cream or suspension preparation containing copper myxin stabilizes the copper myxin therein. More, specifically, this is achieved by the addition of an amount of a water-soluble copper II salt, from a buffer solution containing the salt, i.e., a stabilizer-buffer solution, in an amount sufficient to provide a 2-20% molar excess of copper based on the copper content of copper myxin. Since copper myxin is most stable at a neutral or near neutral pH and since the copper ions of the soluble copper II salt, e.g., copper II acetate, will precipitate as the hydroxide in alkaline solution, the stabilizer-buffer solution is preferably buffered at a pH of 5.7–6.2.

Copper myxin, due to the stabilization of the myxin molecule by chelate formation, is inherently more stable than myxin. In cream and suspension preparations, however, it is necessary to avoid those systems which would promote the dissociation of copper myxin. This dissociation of copper myxin is, in simplified form, as follows:

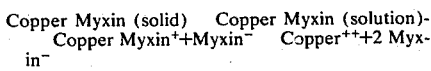

Copper Myxin (solid) ⇌ Copper Myxin (solution) ⇌ Copper Myxin$^+$ + Myxin$^-$ ⇌ Copper$^{++}$ + 2 Myxin$^-$ Therefore, any material which combines, solubilizes or complexes with the copper cations or with the myxin anions can displace the equilibrium to the right and increase the dissociation to the more labile free myxin. In considering the stability of copper myxin in creams or suspensions, the following must be taken into account.

a. pH

In strongly alkaline media, the copper is removed by formation of insoluble cupric hydroxide. In acidic media, with the consequent increased hydrogen ion concentration, the resulting protons compete with the copper. Both these effects cause dissociation of the copper complex to free myxin.

b. Copper Complexing Agents

Appreciable concentrations of ammonia, amines, ethylenediaminetetraacetic acid, citrates, etc. which can, in themselves, complex with copper increase the dissociation of the copper myxin complex.

c. Special Compatabilities of Copper Myxin

Compatability studies on copper myxin with a variety of excipients were carried out with formation of free myxin used as a measure of incompatability. As a result of these studies such well known pharmaceutical excipients as Tween 80 (polyoxyethylene sorbitan monooleate), Span 80, (fatty acid monoester of sorbitan) and stearic acid were found to be incompatible with copper myxin.

d. Packaging Materials

Metals, such as tin and aluminum, act as reducing agents with copper myxin formulations containing a water phase.

e. Multi-phase Systems

Copper myxin dissociation equilibria, as discussed above, become more complex in multi-phase systems. In single phase lipophilic systems, especially if completely non-polar as, for example, petrolatum ointment, there is little if any capability for dissociation into the more labile free myxin so that the system is fairly stable. Single-phase highly polar aqueous systems having little or no solvent capacity for either myxin or copper myxin are also stable. On the other hand, in creams, where a lipophilic-hydrophilic two-phase system exists, several factors complicate copper myxin stability. Copper myxin has a substantial dissociation potential to myxin, expecially in aqueous systems. Degradation of copper myxin, occurs by dissociation in the aqueous phase with subsequent migration of the free myxin to the lipophilic phase where it has an appreciable solubility. The copper ions remain in the aqueous phase where they are more soluble. Hence the migration of free myxin from the aqueous phase causes breakdown of more copper myxin in accordance with the dissociation equations given above.

f. Solvent Systems

Dosage forms with high concentrations of weakly polar solvents capable of dissolving free myxin should be avoided in preparing formulations of copper myxin. This includes high concentrations of propylene glycol, polyethylene glycol etc.

The above detailed difficulties can be minimized by careful consideration of the conditions employed and the materials used in the formulation of pharamceutical preparations.

Hence, in the presence of water or other highly polar solvent, the effect of the addition of a molar excess of cupric ions in depressing the dissociation of copper myxin is of critical importance in formulation evaluation. For example, copper myxin in an aqueous suspension containing 50% propylene glycol and 2.5% polyvinylpyrrolidone has, after centrifuging, a red-pink color in the glycol layer due to partial dissociation of copper myxin to free myxin. This color is instantaneously changed to the greenblack color of copper myxin by the addition of about a 2% molar excess of copper II ions. As noted earlier, free myxin is removed from the aqueous layer by its migration to the lipophilic phase, thus causing more dissociation of copper myxin, in the aqueous phase. Hence, the beneficial effect of the addition of copper ions, in the form of a water-soluble copper II salt, to pharmaceutical preparations containing copper myxin is evident.

A similar effect occurs in a two-phase system. Creams may be either water-in-oil or oil-in-water emulsions. The specific creams used herein, however, are of the oil-in-water type. The surfactants used therein must function not only as emulsifying agents but must also be compatible with copper myxin. In initial investigations, creams were prepared and copper myxin was added, in dispersion, directly to the cream. Free myxin formed immediately, however, due to the greater solubility of myxin in the oil phase of the emulsion as compared to the solubility of copper myxin. In subsequent preparations, copper myxin, dispersed in a stabilizer-buffer solution which contains a water-soluble copper II salt, was added to an aqueous emulsion precursor.

The following examples illustrate the invention.

EXAMPLE 1

This example illustrates the preparation of a stabilizer-buffer solution and its use in the preparation of a dispersion of copper myxin in micronized form.

Stabilizer-buffer solutions of the following compositions are prepared:

| Ingredient | gram/kg of Final Cream | |
|---|---|---|
| | A | B |
| Cupric Acetate Monohydrate | 0.035 | 0.19 |
| Sodium Acetate Trihydrate | 2.041 | 2.041 |
| Acetic Acid, Glacial | 0.05 | 0.05 |
| Water, Distilled, q.s. | 493.0 | 486.7 |

5.5 gram portions of copper myxin, in aggregate form, are added to 100 gram and 170 gram aliquots of stabilizer-buffer solution A and B, respectively. By means of an ultrasonic deaggregation and dispersion technique, not part of this invention but included herein for completeness, the aggregates are rapidly and completely disrupted to fine particles dispersed in the stabilizer-buffer solution. Briefly, the technique involves exposure of the wetted aggregates to vibrations at ultrasonic frequencies. The resulting dispersions are used directly in the preparation of cream formulations.

EXAMPLE 2

This example illustrates the stabilizing effect on copper myxin cream formulations achieved by the addition of excess copper II ions thereto.

The following cream formulations containing copper myxin were prepared.

| Ingredient | Formulation (gram/kg) | | |
|---|---|---|---|
| | II-A | II-B | II-C |
| Copper Myxin | 5.5 | 5.5 | 5.1 |
| Stearyl Alcohol | 170.0 | 170.0 | 170.0 |
| Petrolatum (Petrolatum Perfecta) | 128.0 | 128.0 | 128.0 |
| Fatty acid ester of polyoxyethylene (Myrj 52) | 66.0 | 66.0 | 66.0 |
| Propylene Glycol | 137.5 | 137.5 | 137.9 |
| Hydroxypropylmethylcellulose (Methocel 65 HG 4000) | — | 6.3 | — |
| Distilled Water | — | — | 493.0 |
| Buffer | 493.0 | 486.7 | — |
| % Molar Excess of Copper | 2 | 10 | 0 |

Petrolatum Perfecta, a purified mixture of semi-solid hydrocarbons from petroleum, has a melting point range of 38°–50°C. and an average carbon chain length of 20–22 atoms. Myrj 52 is a partial fatty acid ester of polyoxyethylene. Methocel 65 HG 4000 is Dow Chemical's hydroxypropylmethylcellulose.

The stabilizer-buffer solutions, added to Formulation II-A and II-B above, were from solutions A and B, respectively, as prepared in Example 1, above.

The cream is prepared as follows. The oil phase (stearyl alcohol, petrolatum and Myrj 52) and the water phase (propylene glycol, and the buffer solution without the water-soluble copper salt) are heated, separately, to about 80°C. Thereat, the water phase is added with constant agitation to the oil phase. The resulting cream is cooled to 60°–65°C. and the buffer solution of Methocel 65 HG, heated to 50°C, is admixed therewith. (This solution is prepared by dispersing Methocel 65 HG in an aliquot of the copper-ion free buffer solution at 70°C. using high speed agitation. The dispersion is refrigerated at 5°C. for 12 hours to hydrate the Methocel. The resulting solution is then heated to 50°C. before addition to the emulsion.) The copper myxin dispersion (prepared as in Example 1 above using the buffer solution containing the water-soluble copper salt) is added either when the cream begins to set or at 55°–60°C. Agitation continues until the cream has cooled to room temperature.

Samples from the above formulations were stored at various temperatures for extended periods of time. After such storage, the samples were removed and anlayzed for loss of potency, i.e., degradation of copper myxin to myxin and subsequent reduction of the myxin. Results are tabulated below.

| | Percent Retention of Copper Myxin Activity Formulation | | |
|---|---|---|---|
| | II-A | II-B | II-C |
| After 3 days at 70°C. | 85 | 105 | 72 |
| After 1 month at 45°C. | 115 | 109 | 91 |
| After 2 months at 45°C. | 115 | 109 | 76 |
| After 3 months at 37°C. | 113 | 109 | 74 |
| After 1 month at 55°C. | 116 | 108 | 69 |

EXAMPLE 3

This example illustrates the efficacy of the addition of a 10 and 20 percent molar excess of copper to copper myxin anti-mastitis formulations.

The following formulations were prepared.

| Ingredient | III-A | III-B | III-C | III-D |
|---|---|---|---|---|
| Copper myxin, mg. | 0.588 | 1.18 | 1.05 | 1.75 |
| Polyoxyethylene sorbitan monooleate (Tween 80) mg. | 60.0 | 60.0 | — | — |
| Fatty acid monoester of sorbitan (Span 80), mg. | 40.0 | 40.0 | — | — |
| Hydroxypropylmethylcellulose (Methocel 65 HG 4000), mg. | — | — | 22.5 | 22.5 |
| Benzyl alcohol, ml. | 0.01 | 0.01 | 0.01 | 0.01 |
| Sodium acetate, .3 $H_2O$, mg. | — | — | 2.0 | 2.0 |
| Cupric acetate, .$H_2O$, mg. | — | — | 0.038 | 0.12 |
| Sodium Chloride, mg. | — | — | 8.5 | 8.5 |
| 2% Klucel HA in deionized Distilled $H_2O$ qs | 1.0 ml | 1.0 ml | — | — |
| Deionized distilled $H_2O$ qs | — | — | 1.0 gm | 1.0 gm |
| % Molar excess of copper | — | — | 10 | 20 |

Samples from each formulation were stored at various temperatures for extended periods of time and assayed after storage to determine the loss of copper myxin. The results are tabulated below

| After Storage | % Retention of Copper Myxin Activity III-A | III-B | III-C | III-D |
|---|---|---|---|---|
| at 4°C. for 5 months | — | 69 | — | — |
| at 4°C. for 6 months | 56 | 31 | — | — |
| at 25°C. for 6 months | 50 | — | 101 | 106 |
| at 37°C. for 6 months | — | — | 100 | 105 |
| at 45°C. for 3 months | — | — | 92 | 107 |
| at 55°C. for 1 month | — | — | 88 | 98 |

EXAMPLE 4

This example illustrates the enhancement of stability which is achieved by the use of increased amounts of excess copper.

The following suspensions were prepared

| Ingredient | grams/kg IV-A | IV-B | IV-C (Control) |
|---|---|---|---|
| Copper Myxin | 5.1 | 5.1 | 5.1 |
| Polyvinylpyrrolidone (PVP K-90) | 25.0 | 25.0 | 25.0 |
| Propylene Glycol | 249.9 | 249.9 | 249.9 |
| Buffer Solution | 720.0 | 720.0 | — |
| Distilled $H_2O$ | — | — | 720.0 |

-continued

| Ingredient | grams/kg IV-A | IV-B | IV-C (Control) |
|---|---|---|---|
| Copper Excess (% molar) | 2.0 | 10 | 0 |

PVP K-90 is a trademark of GAR Corp. for a polyvinylpyrrolidone having an average molecular weight of 360,000 and a K-value (calculated according to Fikentscher) of 80–100.

These formulations differed only in the composition of the buffer solutions as listed below

| Ingredient | grams/kg of Formulation Buffer Solution for IV-A | Buffer Solution for IV-B |
|---|---|---|
| Cupric Acetate, .$H_2O$ | 0.035 | 0.175 |
| Sodium Acetate, .$3H_2O$ | 2.041 | 2.041 |
| Acetic Acid, glacial | 0.05 | 0.05 |
| Sodium Chloride | — | 8.5 |
| Water, distilled, q.s. | 720 | 720 |

The formulation were stored at various temperatures for extended periods of time and assayed after storage to determine the loss of copper myxin. Results are tabulated below

| Storage | % Retention of Copper Myxin Activity IV-A | IV-B | IV-C (Control) |
|---|---|---|---|
| Initial at 25°C. | 92 | 101 | 90 |
| 3 days at 70°C. | 81 | 102 | 72 |
| 6 months at 25°C. | 101 | 102 | 80 |
| 1 month at 55°C. | 74 | 102 | 40 |

We claim:

1. A method for the stabilization of pharmaceutical compositions containing an amount of the copper II complex of 6-methoxy-1-phenazinol 5,10-dioxide which is effective as an antimicrobial agent in said composition which comprises adding to the composition a sufficient quantity of a water-soluble copper II salt to provide from about 2 to about 20 percent molar excess of free copper ions based on the copper content in copper myxin, said excess copper ions provided from an aqueous stabilizer-buffer solution containing an amount of the water-soluble copper II salt sufficient to provide the molar excess.

2. The method as in claim 1 wherein the amount of copper salt added provides at least a 2% molar excess of copper.

3. The method as in claim 1 wherein the amount of copper salt added provides a 10% molar excess of copper.

4. The method as in claim 1 wherein the copper salt is cupric acetate monohydrate.

5. The method as in claim 1 wherein the copper salt is added from the aqueous stabilizer-buffer solution comprising, in addition to the copper salt, sodium acetate trihydrate and acetic acid, said stabilizer-buffer solution being at a pH of 5.7 to 6.2

6. A pharmaceutical composition containing, as the active ingredient, an amount of the copper II complex of 6-methoxy-1-phenazinol 5,10-dioxide which is effective as an antimicrobial agent in the composition and, as a stabilizer, from about 2 to about 20 percent molar excess of copper ions based on the copper content in copper myxin, said excess copper ions provided from an aqueous stabilizer-buffer solution containing an amount of a water soluble copper II salt sufficient to provide the molar excess.

7. The pharmaceutical composition as in claim 6 wherein the excess copper is added from the stabilizer-buffer solution comprising a water soluble copper II salt in an aqueous solution buffered at a pH of from 5.7–6.2 by the use of an alkali metal salt having the same anionic moiety as the copper II salt.

8. The pharmaceutical composition as in claim 6 containing, in percents by weight based on the total weight of the composition, 0.5% of the copper II complex of 6-methoxy-1-phenazinol 5,10-dioxide, 0.019% of cupric acetate monohydrate and 0.2% of sodium acetate trihydrate, said cupric acetate monohydrate and sodium acetate trihydrate provided from the aqueous stabilizer-buffer solution.

* * * * *